(12) United States Patent
Guimerà Brunet et al.

(10) Patent No.: US 11,943,548 B2
(45) Date of Patent: Mar. 26, 2024

(54) CIRCUIT FOR THE MULTIPLEXING AND READ-OUT OF VARIABLE-RESISTANCE SENSOR ARRAYS

(71) Applicants: CONSEJO SUPERIOR DE INVESTIGACIONES CIENTÍFICAS (CSIC), Madrid (ES); UNIVERSITAT AUTÒNOMA DE BARCELONA, Bellaterra (ES); FUNDACIÓ INSTITUT CATALÀ DE NANOCIÈNCIA I NANOTECNOLOGIA (ICN2), Bellaterra (ES); INSTITUCIÓ CATALANA DE RECERCA I ESTUDIS AVANÇATS, Barcelona (ES)

(72) Inventors: Anton Guimerà Brunet, Cerdanyola del Valles (ES); Lluis Antoni Terés Terés, Cerdanyola del Valles (ES); Michele Dei, Cerdanyola del Valles (ES); Jose Agustín Cisneros Fernández, Cerdanyola del Valles (ES); Francisco Serra Graells, Bellaterra (ES); José Antonio Garrido Ariza, Sant Just Desvern (ES)

(73) Assignees: CONSEJO SUPERIOR DE INVESTIGACIONES CIENTÍFICAS (CSIC), Madrid (ES); UNIVERSITAT AUTÒNOMA DE BARCELONA, Bellaterra (ES); FUNDACIÓ INSTITUT CATALÀ DE NANOCIÈNCIA I NANOTECNOLOGIA (ICN2), Bellaterra (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 486 days.

(21) Appl. No.: 17/264,426

(22) PCT Filed: Aug. 2, 2019

(86) PCT No.: PCT/EP2019/070868
§ 371 (c)(1),
(2) Date: Jan. 29, 2021

(87) PCT Pub. No.: WO2020/025786
PCT Pub. Date: Feb. 6, 2020

(65) Prior Publication Data
US 2021/0321053 A1 Oct. 14, 2021

(30) Foreign Application Priority Data
Aug. 3, 2018 (EP) .................................. 18382593

(51) Int. Cl.
*H04N 25/40* (2023.01)
*H03D 3/00* (2006.01)
(Continued)

(52) U.S. Cl.
CPC ............ *H04N 25/40* (2023.01); *H03D 3/007* (2013.01); *H04N 25/74* (2023.01); *H04N 25/75* (2023.01);
(Continued)

(58) Field of Classification Search
CPC ...... A61B 2562/0217; A61B 2562/046; G01N 27/414; G01N 27/4148; H04N 25/40;
(Continued)

(56) References Cited

U.S. PATENT DOCUMENTS 7,129,465 B2   10/2006   Garcia et al.
2011/0199106 A1*  8/2011   Lotto ................... H04N 25/616
                                              324/649
(Continued)

FOREIGN PATENT DOCUMENTS

WO   WO/2016/100049 A1   6/2016

OTHER PUBLICATIONS

Hébert, Clement, et al. "Flexible graphene solution-gated field-effect transistors: efficient transducers for micro-electrocorticography." Advanced Functional Materials 28.12: 1703976, First published Nov. 13, 2017. (Year: 2017).*
(Continued)

*Primary Examiner* — Ryan Johnson
(74) *Attorney, Agent, or Firm* — Peter B. Scull

(57) ABSTRACT

An apparatus and a method using no switching elements for multiplexing and reading arrays of sensors whose electrical
(Continued)

resistance is modulated by the signals to be measured are proposed. Sensor elements are arranged in groups and columns where each column is fed with a continuous voltage waveform of different amplitude, frequency and phase characteristics which then produce current signals that are modulated by the variable resistance signals to be measured. Modulated currents are summed row-wise and collected at the read-out circuits, either by applying a constant voltage to each row of the array or by connecting a capacitor and converting these current summations into output voltage signals. The read-out circuits de-multiplex each individual sensor signal to be measured by lock-in demodulation according to the frequencies and phases employed for the stimulation of each column.

20 Claims, 7 Drawing Sheets

(51) Int. Cl.
*H04N 25/74* (2023.01)
*H04N 25/75* (2023.01)
*H04N 25/76* (2023.01)

(52) U.S. Cl.
CPC ........ *H04N 25/76* (2023.01); *A61B 2562/046* (2013.01)

(58) Field of Classification Search
CPC ........ H04N 25/74; H04N 25/75; H04N 25/76; H03D 3/007
See application file for complete search history.

(56) References Cited

U.S. PATENT DOCUMENTS

| | | | |
|---|---|---|---|
| 2016/0038053 A1* | 2/2016 | Bohorquez | A61B 5/053 600/393 |
| 2016/0364078 A1 | 12/2016 | Krah et al. | |
| 2017/0219519 A1* | 8/2017 | Chen | G01R 27/02 |
| 2019/0162695 A1* | 5/2019 | Lu | H01L 29/73 |

OTHER PUBLICATIONS

ISR and Written Opinion, PCT App No. PCT/EP2019/070868, dated Aug. 17, 2019, pp. 1-13, ISA, European Patent Office, 2280 HV Rijswijk, NL.

* cited by examiner

CIRCUIT FOR THE MULTIPLEXING AND READ-OUT OF VARIABLE-RESISTANCE SENSOR ARRAYS

FIELD

Disclosed are sensor arrays and demultiplexing and demodulating signals from sensor arrays.

BACKGROUND

There is an increasing interest in advanced read-out systems capable of managing multiple sensors simultaneously in order to extract high-level information features from the temporal and spatial identification of data patterns in the combined outputs of the multiple sensors, as in sensor arrays. Modern examples of these smart sensing applications are vision systems for autonomous navigation, lab-on-a-chip platforms of biosensors for health monitoring or implantable devices for massive neural recording.

FIG. 1 illustrates a known sensor array with switching elements and logic for multiplexing and demultiplexing sensor signals. Massive sensory systems demand large-scale arrays of sensors arranged in bi-dimensional grids (1) easily exceeding hundreds or thousands of recording sites. In this context, micro- and nano-technologies play a key role when it comes to miniaturizing the size and to decreasing the manufacturing costs associated with the fabrication of these sensing arrays. For this reason, integrated circuit (IC) technologies are the common choice for the physical implementation of the electronic frontend in charge of supplying the large amount of read-out channels required.

In the core of such read-out systems, the individual sensors are progressively evolving from merely passive structures (e.g. electrodes) to active devices (e.g. transistors), which can provide very early amplification for the purpose of improving signal integrity and system sensitivity. In general, most of these active sensors can be modeled at first instance as variable-resistance devices (2), whose current conduction is modulated by the voltage signal to be measured (3).

In this scenario, the classic point-to-point connection between each active sensor and a dedicated read-out circuit is prohibitive for large-scale arrays due to two practical limitations. On the one hand, the pin-out count of ICs cannot be scaled up easily without incurring high packaging costs, so hybrid array-IC implementations tend to suffer from a limited number of read-out channels available. On the other hand, if monolithic array-IC arrangements are employed to integrate all this point-to-point connectivity, then strong limitations arise regarding overall sensing area due to the own cost and yield figures of IC technologies. Hence, some multiplexing is mandatory between the massive array of active sensors and the read-out IC in charge of processing the huge amount of signals to be measured.

Known approaches address the above large-scale array-IC multiplexing requirements by introducing a switching element (4) for each active sensor (2) of the array (1). These switches (4) allow the alternate connection of several active sensors (2) to the same row output (5) of the array (1). Each row output (5) is in turn connected to the corresponding analog input channel of the read-out IC frontend (6). In order to further reduce the overall array-IC connectivity, all switches (4) of the same column of the array (1) share the same selection input (7). Each column selection input (7) is connected to the corresponding digital output channel of the multiplexer (8), which can be integrated together with the read-out frontend (6).

The principle of operation of known approaches to multiplexing is as follows. First, the multiplexer (8) activates a single column of switches (4) through the corresponding digital control signal (9) while keeping the rest of column inputs (7) unselected. After the selected switches (4) are closed, the current (10) modulated by the voltage signal to be measured (3) of each selected variable-resistance sensor (2) is read out in parallel by the analog input channels of the IC frontend (6) through each row output (5) of the array (1). The rest of variable-resistance sensors (2) connected to the same row output (5) cannot not contribute to this current because their respective series switches (4) remain open. Once the read-out process is completed, the multiplexer (8) disables the referred column of switches (4). At this point, the system restarts the same cycle of operation but for the next column selection line (7) until completing the column-wise sequential scanning of the entire array (1). Indeed, this multiplexing strategy is implementing a time-division multiple access (TDMA) mechanism. In this sense, further TDMA multiplexing between the row outputs (5) of the array (1) can be also performed inside the read-out IC frontend (6).

In practice, several drawbacks can arise due to the use of TDMA multiplexing between large-scale arrays of variable-resistance sensors and their corresponding read-out circuits.

First, there is the requirement of including two devices in each recording site of the array (1), one for sensing (2) and the other one for multiplexing purposes (4). This fact tends to enlarge the pitch of the grid with the consequent penalties in terms of spatial density. Also, in the case that the two devices (2,4) cannot be effectively built through a single physical process, this limitation may also increase the overall complexity of the technology needed to integrate the full active array (1).

Second, the planar metallization technologies employed to physically implement the routing of the connectivity inside the bi-dimensional sensing array (1) usually imply some crossings between the column lines (7) coming from the digital multiplexer (8) and the row lines (5) going to the read-out circuits (6). Typically, the logical levels of the digital signals (9) travelling through these column lines (7) can easily exceed 1V, while the effective current signals (10) collected through the row lines (5) are transduced from low-level analog signals (3), which can be as weak as a few μV in amplitude for some applications (i.e. six orders of magnitude lower). Hence, ensuring proper decoupling between the control and the reading lines of the array (1) can be a clear design bottleneck. In some cases, the only viable solution may be increasing the gain of the current-to-voltage converters located at the input of the read-out circuits (6), with the consequent penalties in terms of area and power consumption.

Third, the intrinsic discrete-time operation of the TDMA multiplexing, together with the unavoidable technology mismatch between the variable-resistance sensors (2) of the array (1), can introduce non-negligible artifacts at the output current waveforms (10). These undesired transients signals may be generated at each time slot of the scanning process and they are usually originated by differences in direct-current (DC) characteristics between sensors (2) due to technology deviations along the array (1). Eventually, such artifacts can even saturate the input stage of the read-out circuits (6) when trying to measure very weak signals.

Fourth, the signal waveforms (10) exiting the active array (1) through each row output (5) are in the current domain. This fact usually imposes a DC coupling to the input of the read-out circuits (6). Hence, the noise contributions of such read-out circuits (6) can easily degrade the signal integrity at low frequencies, where the sensing bandwidth of interest is usually located. In order to mitigate such signal-to-noise losses, correlated double sampling (CDS) techniques are usually required at the read-out circuits (6), with the consequent impact on area and power consumption.

There may thus be a desire for or desiderata to find a solution or solutions or arrangements to multiplex and demultiplex signals from sensor elements in sensor arrays that (i) does not use switching elements that increase complexity and take up silicon chip real estate, (ii) minimizes or eliminates coupling between week signals to be measured, (iii) minimizes or eliminates artifacts caused by switching elements, and/or (iv) minimizes or eliminates DC coupling to the input of the read-out circuits.

SUMMARY

The present solution or solutions and/or disclosures hereof relate to an apparatus and/or a method for multiplexing and reading arrays of sensors whose electrical resistance is modulated by the signals to be measured. According hereto, the sensors are arranged in a bi-dimensional array so that their terminals are grouped column- and row-wise. Independent voltage sources are applied to each column of the array in order to stimulate harmonic waveforms of different amplitudes, frequencies and phases. For each sensor, the corresponding column harmonic voltage waveform is mixed with the variable-resistance signal to be measured generating a modulated current waveform.

These modulated currents are summed row-wise and collected at the read-out circuit, either by applying a constant voltage to each row of the array or by connecting a capacitor and converting these current summations into output voltage signals. Finally, the read-out circuit demultiplexes each individual sensor signal to be measured by lock-in demodulation according to the frequencies and phases employed for the stimulation of each column.

The disclosures hereof do not require any switching element in the array to perform the sensor multiplexing. Also, the generation of artifacts is strongly reduced due to its continuous-time waveform operation compared to discrete-time scanning techniques. Moreover, the use of frequency and phase lock-in demodulation during de-multiplexing strongly reduces the equivalent noise bandwidth of the overall read-out system. Furthermore, the low-frequency noise contributions added by the read-out circuits can be filtered out through the appropriate selection of frequencies for each column of the array.

Finally, a novel method for manufacturing the sensor array is presented. The method uses GFET transistors.

DETAILED DESCRIPTION

Figure 1:
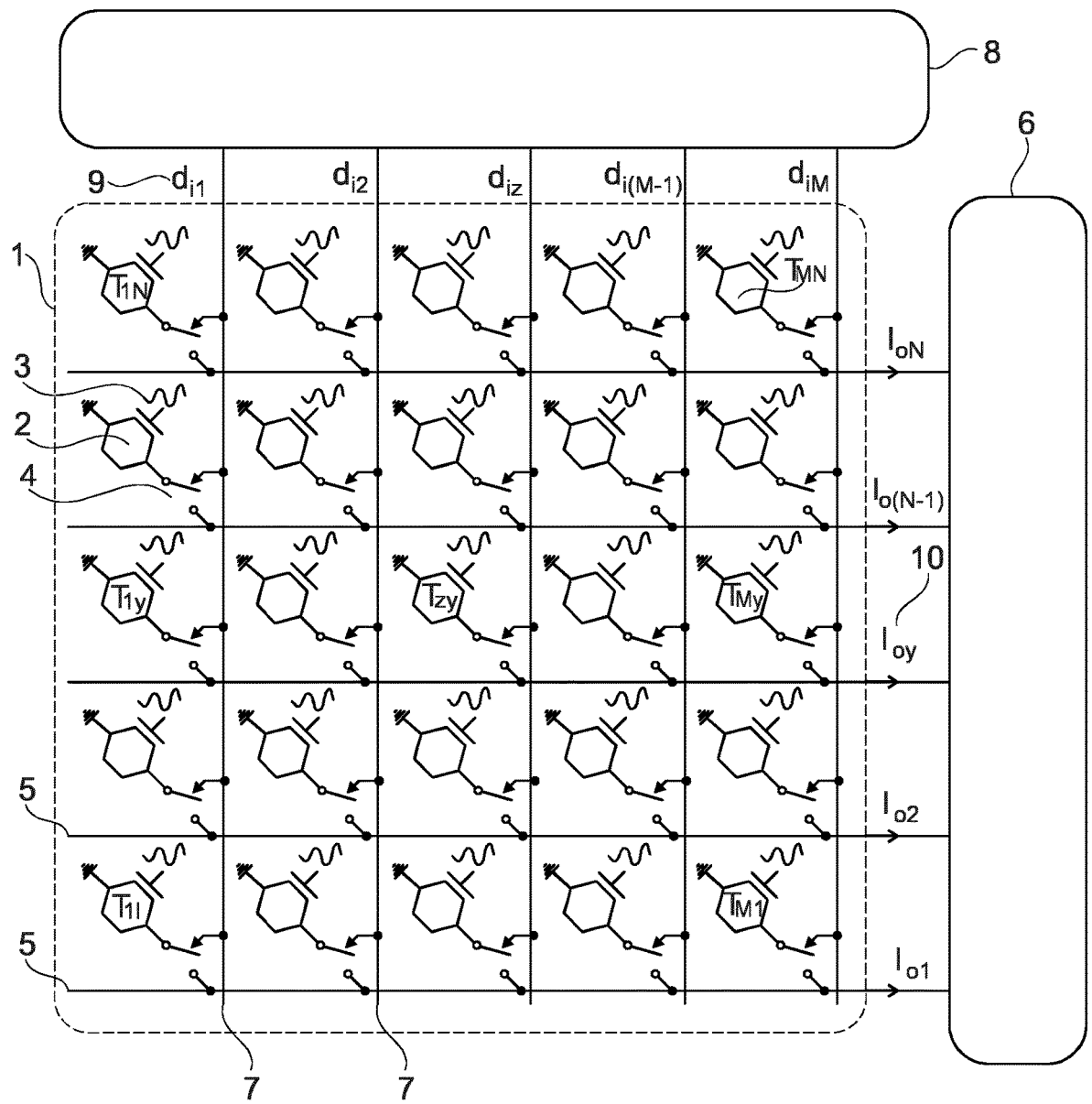
FIG. 1 illustrates a known sensor array with switching elements and logic for multiplexing and demultiplexing sensor signals.

The word "exemplary" is used herein to mean "serving as an example, instance, or illustration". Any implementation described herein as "exemplary" is not necessarily to be construed as preferred or advantageous over other implementations.

The terms "component" and "element" or their plural form may be used interchangeably where combined with other words (e.g. "sensor") and refer to the same element(s).

The symbol "Ag/Cl" is intended to mean "Silver Chloride".

The acronym "Correlated Double Sampling" is intended to mean "CDS".

The acronym "DC" is intended to mean "Direct Current".

The acronym "FDMA" is intended to mean "Frequency-Division Multiple Access".

The acronym "GFET" is intended to mean "Graphene-based solution Gate Field Effect Transistor".

The acronym "OpAmp" is intended to mean "Operational Amplifier".

The acronym "TDMA" is intended to mean "Time Division Multiple Access".

The term "mobile device" may be used interchangeably with "portable device" and "device with wireless capabilities".

The following terms have the following meanings when used herein and in the appended claims. Terms not specifically defined herein have their art recognized meaning.

"SU-8" is a commonly used epoxy-based negative photoresist.

A "lock-in amplifier" is a type of amplifier that can extract a signal with a known carrier wave from an extremely noisy environment.

"Modulation" is the process of varying one or more properties of a periodic waveform, called the carrier signal, with a modulating signal that typically contains information to be transmitted.

"Demodulation" is the process of extracting the original information-bearing signal from a carrier wave.

"Multiplexing" is a method by which multiple analog or digital signals are combined into one signal over a shared medium.

"Demultiplexing" is a method by which the original analog or digital signals are extracted from a combined (or multiplexed) signal containing the original signals.

"Lift-off process" in microstructuring/microelectronics technology is a method of creating structures (i.e. patterning) of a target material on the surface of a substrate (e.g. a wafer) using a sacrificial material (e.g. Photoresist). It is an additive technique as opposed to more traditional subtracting technique like etching. The scale of the structures can vary from the nanoscale up to the centimeter scale or further, but are typically of micrometric dimensions.

The disclosures and/or solutions hereof allow the multiplexing of sensors in sensor arrays while eliminating the need to use switching elements (like in Time Division Multiple Access (TDMA) solutions), which increase the complexity and cost of design and fabrication of sensor arrays, while introducing noise and artifacts that can seriously affect the accuracy of the sensor signals especially where very low voltage signals need to be multiplexed. As a consequence, the disclosures and/or solutions also allow the simplification of sensor array design by eliminating the need to add complex auxiliary circuits (e.g. for de-noising) or for handling larger voltages and can be used in modern portable devices where low energy consumption is a prerequisite.

Figure 2:
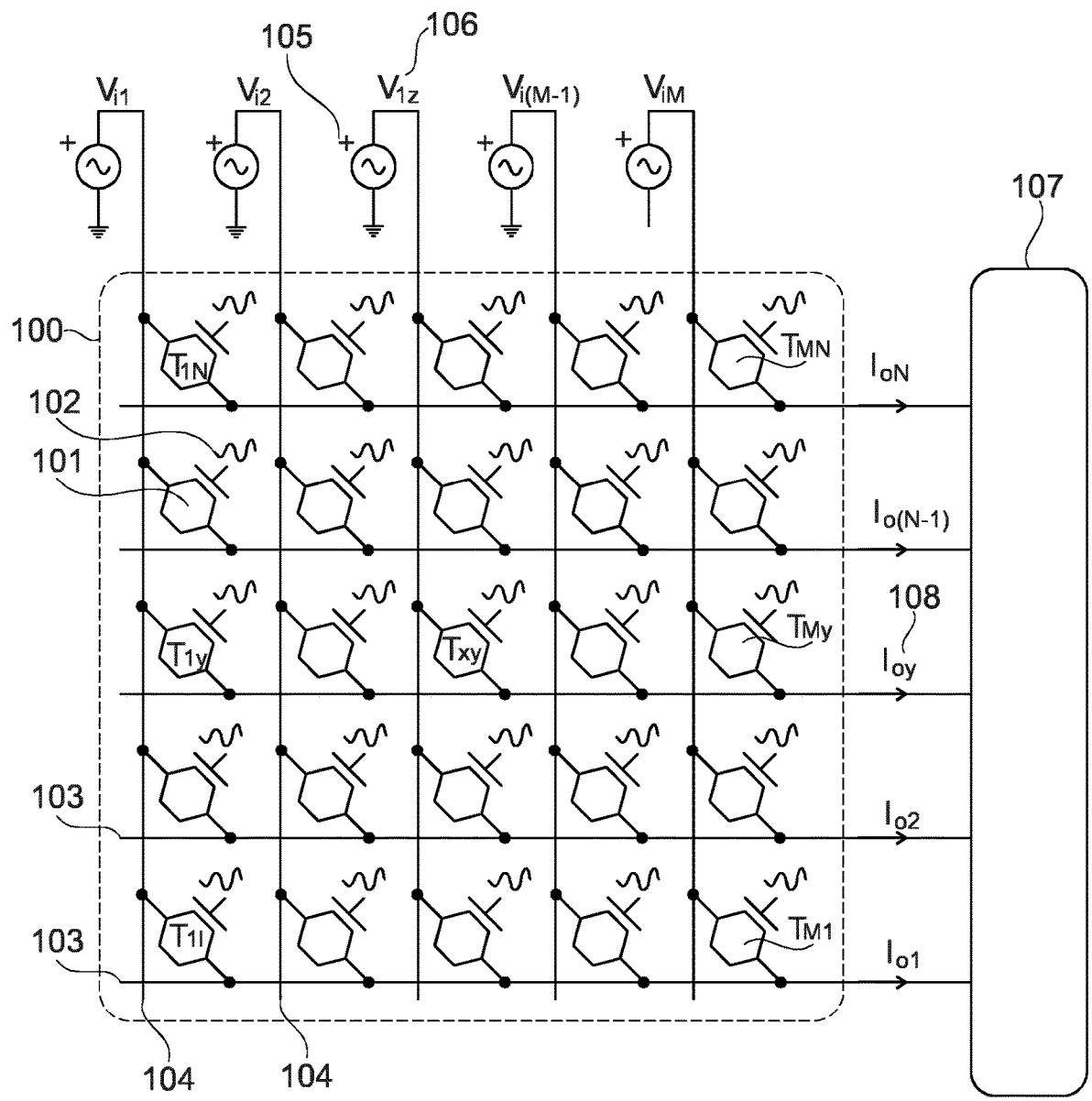
FIG. 2 illustrates an exemplary sensor array with logic for multiplexing and demultiplexing sensor signals.

FIG. 2 illustrates an exemplary sensor array with logic for multiplexing and demultiplexing sensor signals.

Sensor array 100 is a bi-dimensional array of sensors 101, where the electrical resistance of each sensor in the array is modulated by the signals to be measured 102. By example, the sensor array may be an image sensing array like the one used in digital camera. An artisan skilled in related art understands that the sensor array is not limited to this example but may be of any type, any shape, and contain sensor elements of any type making use of any technology available. In one aspect the sensing elements in the sensor array may all be of identical type and characteristics, while in another aspect the sensing elements may be of various types and characteristics.

Each sensing element 100 has two output terminals, which terminals are connected to a row line 103 and a column line 104, respectively. The arrangement of sensors 101 inside array 100 ensures that there is a unique combination of columns and rows associated to each individual sensor 101. For example, the sensor highlighted with the numeral 101 in the FIG. 2 is associated with the $1^{st}$ column (counting from the left) and with the $2^{nd}$ row (counting from the top). Similarly for all the other sensors in array 100.

Independent voltage sources 105 are connected to each column 104 of array 100 in order to stimulate continuous-time harmonic voltage waveforms 106 ($V_{i,j}$, where j is the column number in array 100). The amplitudes, frequencies and phases of voltage waveforms $V_{i,j}$ 106 can be selected independently so as enable supplying a voltage waveform of precisely know characteristics to each column of array 100. In one aspect each column is fed with a continuous-time harmonic voltage waveforms 106 which has at least one of its three characteristics (amplitude, frequency and phase) different from the characteristics of the continuous-time harmonic voltage waveform 106 supplied to any other column of array 100.

Row lines 103 of array 100 are connected to the corresponding analog inputs of frontend circuits 107. As a result, frontend circuits 107 can read the summation of currents 108 (Io,i, where i is the row number in array 100) collected by each row line 103 in parallel.

The principle of operation for the multiplexing and readout of each signal to be measured 102 is as follows. For each sensor 101 of array 100, the corresponding column harmonic voltage waveform $V_{i,j}$ 106 is locally mixed at sensor 101 with the signal to be measured 102 by the variable-resistance behavior of sensor 101. As a result, a modulated current waveform is permanently conducted by each sensor 101, which modulated current waveform incorporates the harmonic components of the corresponding column voltage waveform $V_{i,j}$ 106 modulated in amplitude by its particular signal to be measured 102.

All the individually modulated currents of each sensor 101 connected to the same row line 103 are summed in continuous time to generate the corresponding row output current $I_{o,i}$ 108. Indeed, each row current waveform Io,i 108 contains the entire collection of harmonics used in every column voltage waveform $V_{i,j}$ 106, where each column voltage waveform $V_{i,j}$ is modulated in amplitude by the individual signal to be measured 102 of corresponding sensor 101. The multiplexing mechanism of sensor array 100 is, in essence, a Frequency-Division Multiple Access (FDMA) mechanism.

Frontend circuits 107 read in parallel all row output FDMA current waveforms Io,i 108 and de-multiplex each individual sensor signal to be measured 102 by lock-in demodulation according to the amplitudes, frequencies and phases employed in harmonic voltage waveform $V_{i,j}$ 106 of each column line 104 of the entire array 100.

Figure 3:
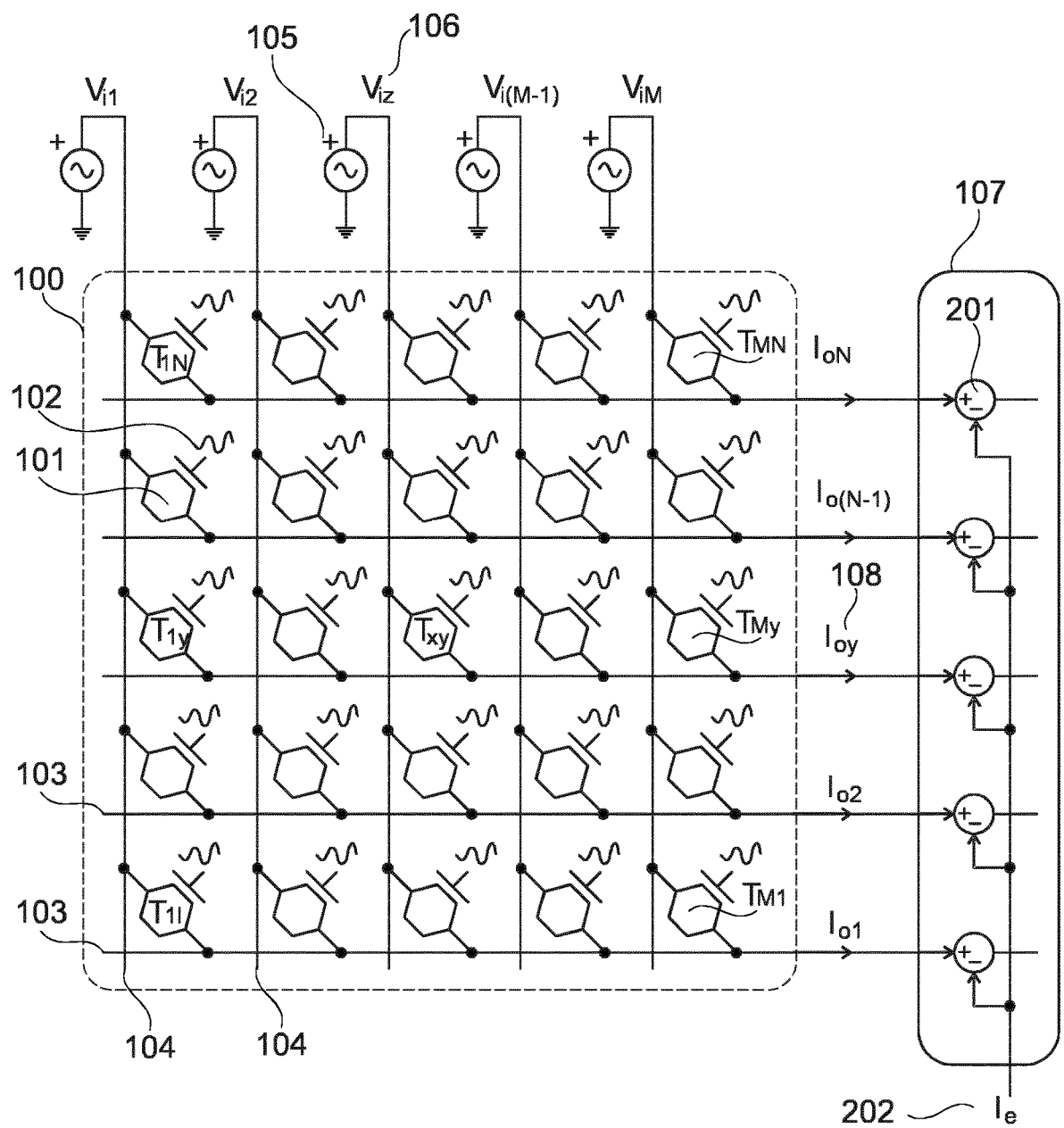
FIG. 3 illustrates an exemplary implementation of a sensor array with logic subtracting common signal components from row output currents for demultiplexing measured signals.

FIG. 3 illustrates an exemplary implementation of a sensor array with logic subtracting common signal components from row output currents for demultiplexing measured signals. Sensor array 100, sensors 101, and voltage sources 105 used for signal modulation in FIG. 3 are identical and identically interconnected as those in FIG. 2.

In the alternative exemplary implementation of FIG. 3, the amplitudes of the signals to be measured 102 by sensors 101 are very weak compared to the amplitudes of column harmonic voltage waveforms $V_{i,j}$ 106. For this reason frontend circuits 107 are designed to subtract 201 all the common signal components $I_c$ 202 (that have not been modulated by individual signals 102 at each sensor 101) from every row output FDMA current Io,i 108 before the de-multiplexing process. This subtraction operation prior to the demultiplexing of row output FDMA current Io,i 108 allows the removal of noise from Io,i and alleviates the need for complex circuits (e.g. bandpass filters, etc.) inside frontend circuits 107.

The parallel read-out of the row output FDMA current waveforms Io,i 108 can be performed in different ways by frontend circuits 107.

Figure 4:
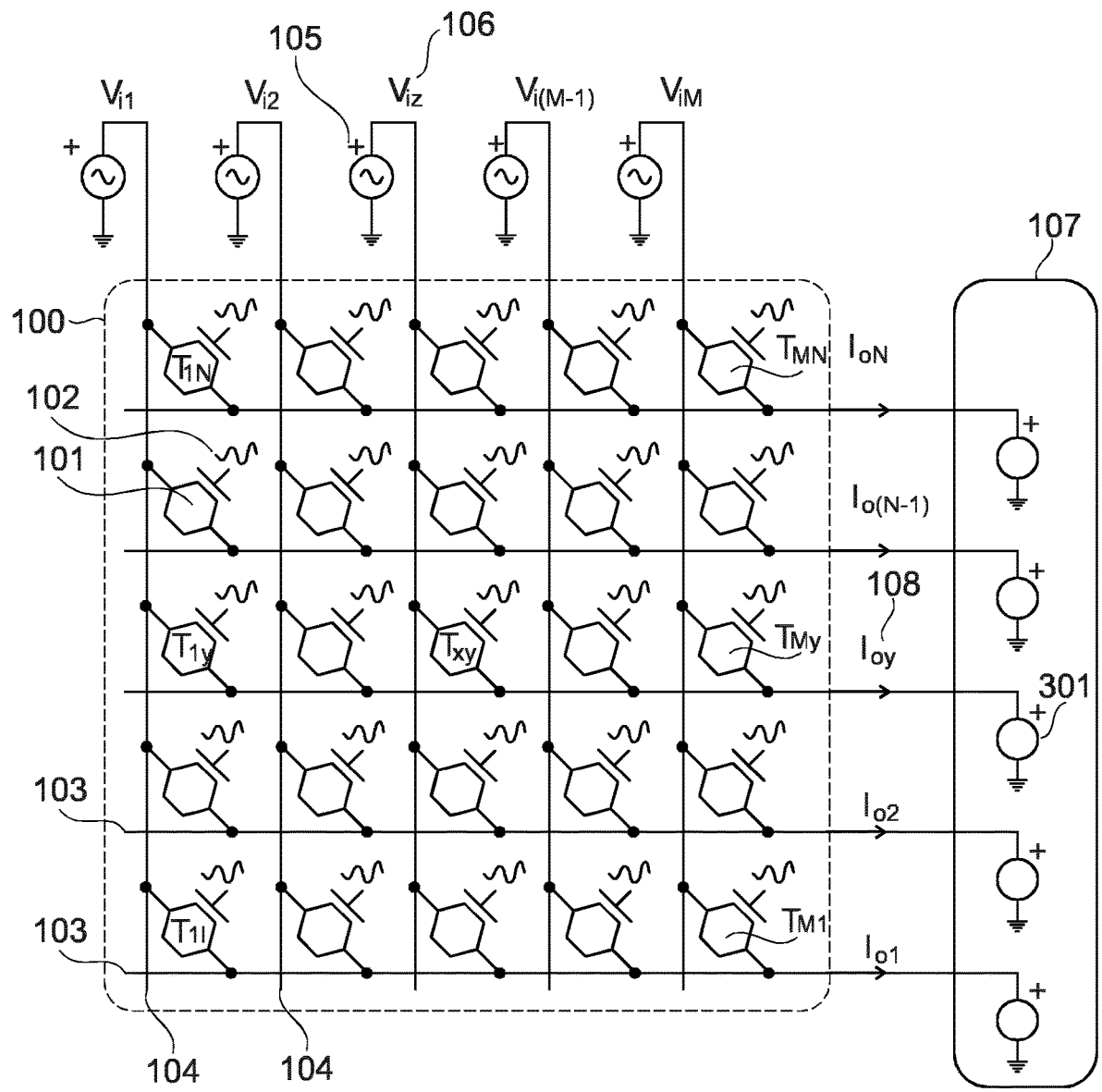
FIG. 4 illustrates an exemplary implementation of a sensor array with logic using constant voltages for demultiplexing measured signals.

FIG. 4 illustrates an exemplary implementation of a sensor array with logic using constant voltages for demultiplexing measured signals. Sensor array 100, sensors 101, and voltage sources 105 used for signal modulation in FIG. 4 are identical and identically interconnected as those in FIG. 2.

In the exemplary implementation of FIG. 4, a constant voltage 301 is applied at each row of array 100. For any row line 103, current Io,I 108 demanded by all sensors 101 in row line 103 is drained or sourced through frontend circuits 107.

In one aspect, constant voltage 301 applied to each row of 103 of array 100 is the same for all rows 103.

In another aspect, a first constant voltage is applied to the first row, a second constant voltage is applied to the second row, and so on.

Figure 5:
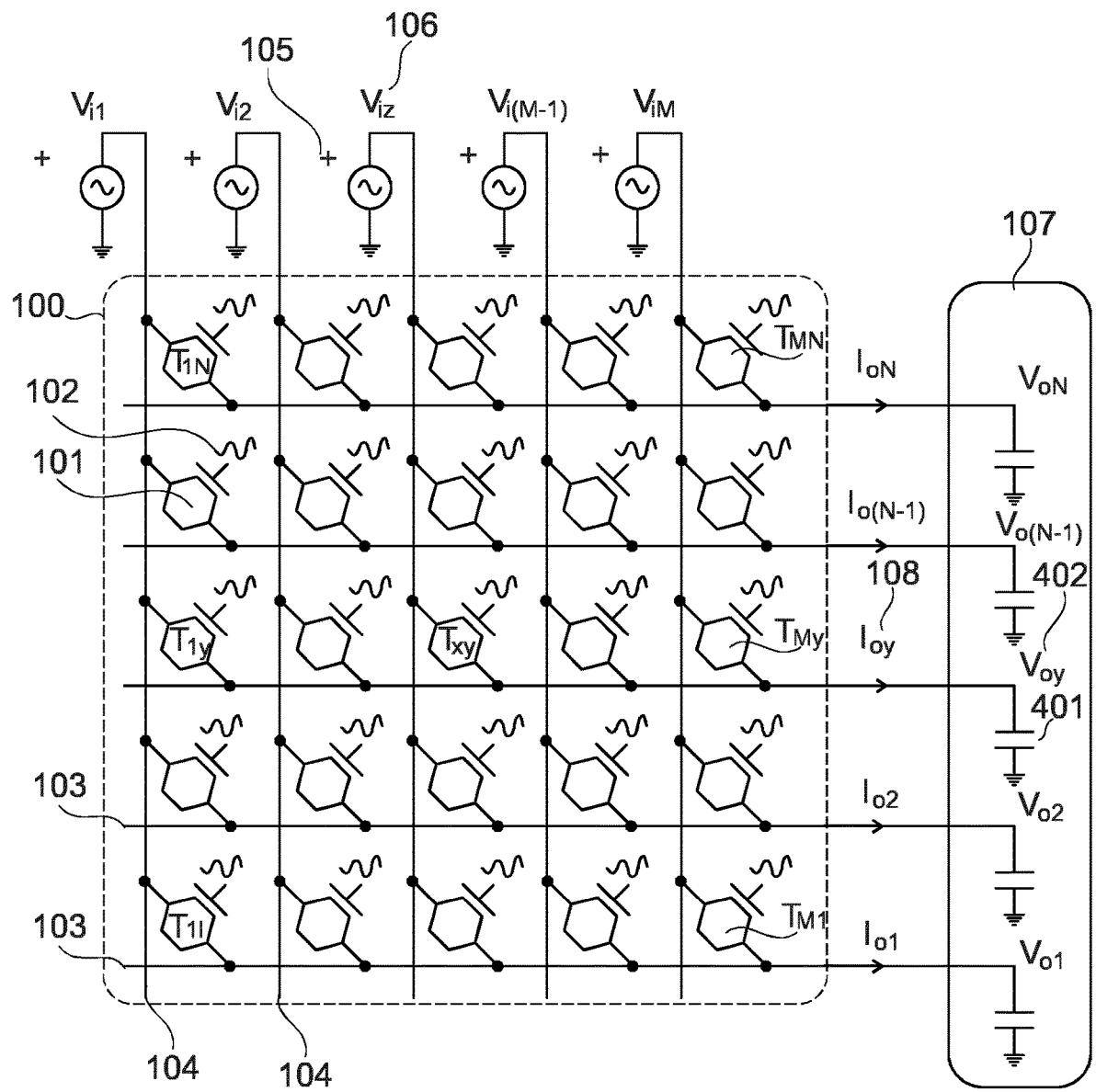
FIG. 5 illustrates an exemplary implementation of a sensor array with logic using capacitors for demultiplexing measured signals.

FIG. 5 illustrates an exemplary implementation of a sensor array with logic using capacitors for demultiplexing measured signals. Sensor array 100, sensors 101, and voltage sources 105 used for signal modulation in FIG. 5 are identical and identically interconnected as those in FIG. 2.

In the exemplary implementation of FIG. 5 a capacitor 401 is connected to each row of array 100, so that the FDMA current summation Io,I 108 is integrated and converted into an output row voltage signal Vo,I 402 that is measured by frontend circuits 107.

In one aspect, capacitors 401 of the same type and characteristics are connected to each row 103 of array 100.

In another aspect, a first capacitor of a first type and first characteristics is connected to the first row, a second capacitor of a second type and second characteristics is connected to the second row, and so on.

Concerning column harmonic voltage waveforms 106, several configuration profiles can be chosen for their amplitude, frequency and phase.

In one exemplary implementation, regarding the amplitude of column harmonic voltage waveforms 106, high-amplitude levels are selected for allowing more output signal gain at row FDMA output current Io,I 108 for the same input signal to be measured 102. However, high amplitude voltages bring the penalty of having more power consumption dissipated in array 100. This is a serious problem as battery levels in portable devices may drop faster than is acceptable, electronics in the devices hosting array 100 and in array 100, itself, get heated up resulting in damage over time and risk of burnout. If high amplitude voltages are used, electronics in array 100 must be designed to withstand higher voltage, resulting in higher complexity and design and manufacturing costs, while at the same time noise may be introduced in the multiplexed modulated currents Io,I 108, which, in turn, necessitates the use of additional denoising logic, which increases complexity, and costs, and limits the amount of sensor elements 101 that can be packed per cm$^2$ of silicon chip real estate.

In another exemplary implementation, the amplitude parameter may be used for disabling all sensors 101 connected to a given column line 104 by simply keeping that column voltage $V_{i,j}$ 106 at a fixed Direct Current (DC) value.

Different frequency values may be allocated for each column harmonic voltage waveform $V_{i,j}$ 106 in order to ensure proper FDMA operation, with enough channel frequency spacing to avoid crosstalk between the spectra of the sensor signals to be measured 102. As for the phase of each column harmonic voltage waveform $V_{i,j}$ 106, 90-degree orthogonal configurations with in-phase (I) and quadrature (Q) separated in two column waveforms 106 may be selected for reusing the same frequency voltage waveform.

In yet another exemplary implementation, a special case of the above configuration profiles for column harmonic voltage waveforms $V_{i,j}$ 106 may be used. This exemplary implementation uses the differential reading between two signals to be measured 102 of the same row 103 by using the same amplitude, the same frequency and inverting the phase of one voltage waveform $V_{i,j}$ 106 when stimulating two respective columns 104.

Sensor Element Design and Manufacturing

Sensor array 100 may be designed to contain any type of sensor elements according to the desired sensing application and to the choice of sensing principle of operation and sensing technology.

By example and without limiting the scope of use or of implementation of the present exemplary developments, a Graphene-based solution Gate Field Effect Transistor (GFET) device may be used. GFETs may be used to obtain a current waveform modulated by a signal applied at the gate terminal (i.e. an electrode immersed in an electrolyte), thereby, allowing the GFET to operate as mixer.

Figure 6:
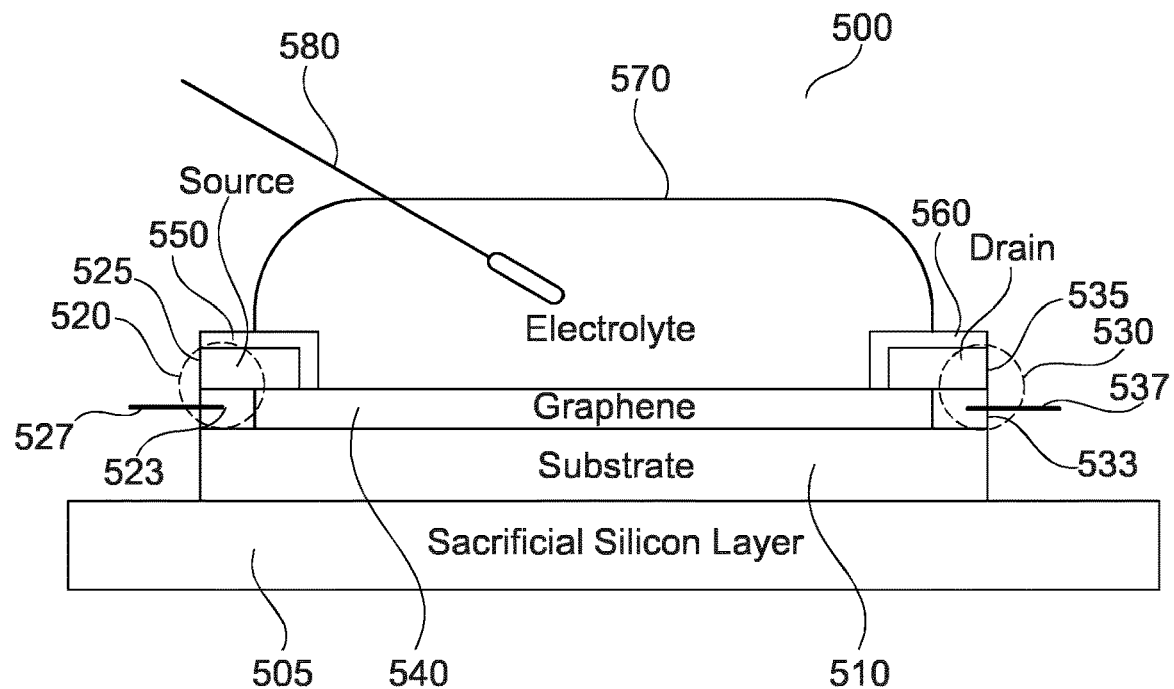
FIG. 6 shows a schematic representation of a GFET device.

FIG. 6 shows a schematic representation of a GFET device. Such a GFET device 500 may be fabricated by a series of steps, commencing with depositing a flexible polyimide substrate polymer layer 510 on a sacrificial silicon wafer 505 (i.e. a silicon wafer that will be removed, e.g. by an etching or other process). To improve the resistivity of the contacts of sensor 500, a first layer of metallic tracks 523, 533 is defined by a lift-off technique. Then a single graphene layer 540 is transferred from a growth substrate onto polyimide substrate layer 510. In order to define the shape of the transistor channel, graphene layer 540 is etched by oxygen plasma. A second metal layer is deposited and defined into tracks 525, 535 by lift-off techniques. Metal tracks 523 and 525 are in direct contact with each other and form the transistor's source 520, while metal tracks 533, 535 are in direct contact with each other and form the transistor's drain 530. External source 527 and drain 537 electrodes may also be added in exemplary implementations.

The active area on the transistor channel is defined by an SU-8 insulation layer defined into two insulator parts 550, 560 deposited on the transistor's source 520 and drain 530. GFET fabrication is finished by defining polyimide substrate 510 by reactive ion etching, depositing an electrolyte 570 on the transistor's side opposite substrate 510, and positioning an Ag/Cl electrode 580 inside electrolyte 570. Electrode 580 forms the base of transistor 500.

Figure 7:
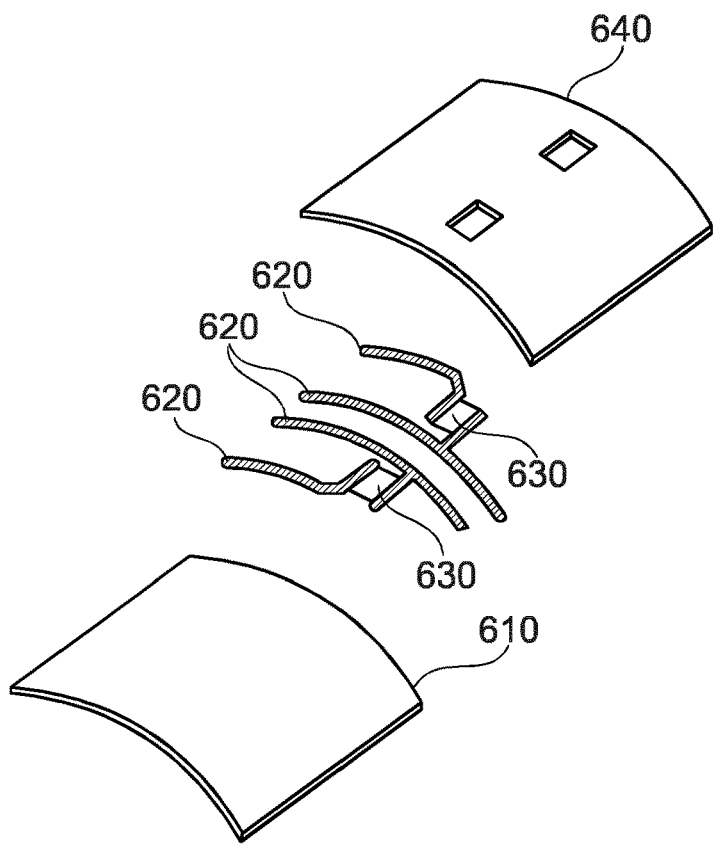
FIG. 7 shows an exploded view of the fabrication layers of a GFET device.

FIG. 7 shows an exploded view of the fabrication layers of a GFET device. GFET device 600 is made of a polymer substrate layer 610, a layer of metal contacts 620 forming source 520 and drain 530, and an insulation layer 640. In between metal contacts 620 is positioned grapheme channel 630.

Example GFET Connection for Lock-in Demodulation

Figure 8:
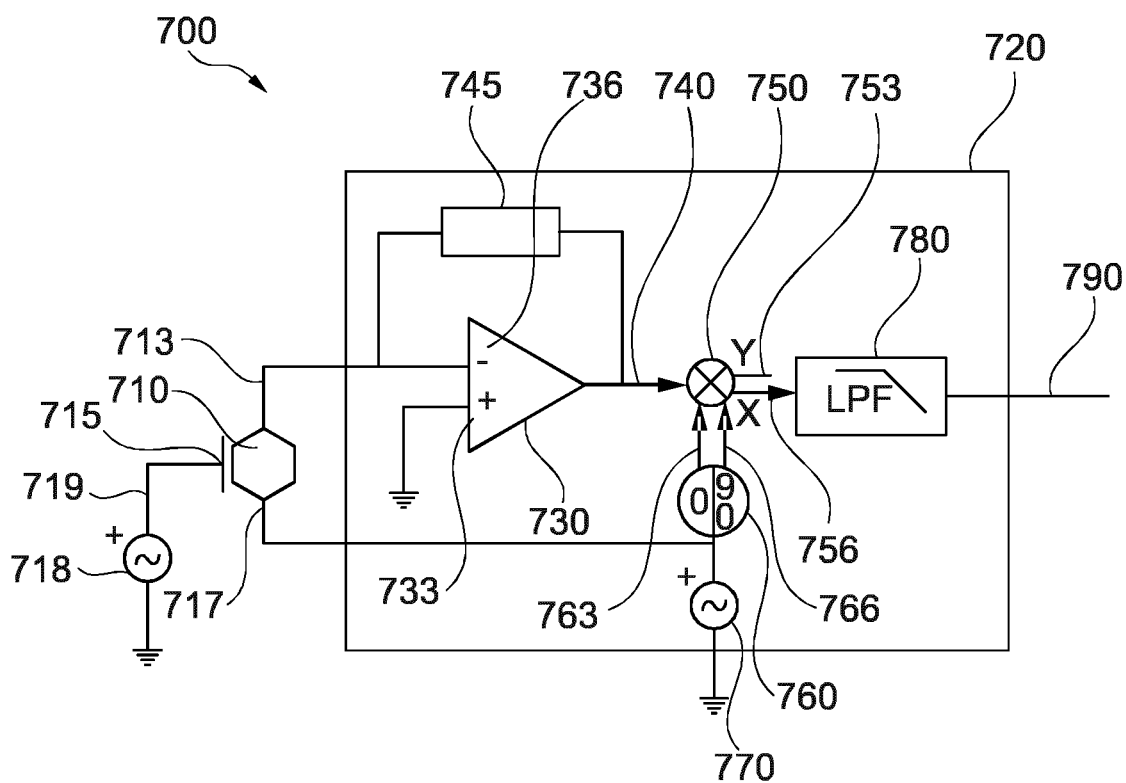
FIG. 8 shows an electronic circuit diagram example for demodulating modulated signals from a GFET transistor device.

FIG. 8 shows an electronic circuit diagram example for demodulating modulated signals from a GFET transistor device. Demodulation circuit contains, among other components, GFET device 710, and lock-in amplifier 720.

Lock-in amplifier 720 is composed of an Operational Amplifier (OpAmp) 730 whose positive input 733 is grounded, and negative feedback is achieved by connecting OpAmp's 730 output 740 to OpAmp's 730 negative input 736 via a resistor 745. OpAmp's 730 output 740 is also connected to a mixer/multiplier device 750.

Voltage carrier source device 770 produces a carrier signal. Voltage carrier source device 770 is grounded at one end and connected at the other end to GFET's 710 source terminal 717 and to a phase shifter device 760. Phase shifter device 760 outputs an in-phase (I) signal 763 (i.e. the carrier signal) and a quadrature (Q) signal 766 (i.e. the carrier signal shifted by 90°). Both (I) and (Q) signals are fed to mixer/multiplier device 750, which mixer/multiplier device 750 produces an "X" signal (at 90°) 756 and a "Y" signal (at 0°) 753. The "X" signal (at 0°) 756 is fed to a LowPass Filter (LPF) 780 which LPF 780 rejects high frequencies from its input signal and produces output signal 790.

GFET device 710 has its source terminal 717 fed with the carrier signal from voltage carrier source device 770, and its electrolytic gate 715 fed with the signal to be measured 719 through an Ag/Cl electrode. GFET 710 modulates the carrier signal (that is applied to its source terminal 717) with the signal to be measured (that is applied to its electrolytic gate terminal 715) and outputs the modulated signal (via its drain terminal 713, which is virtually grounded) to OpAmp's 730 positive terminal 736.

Output signal 790 is substantially identical to the signal to be measured 719.

In an example and in no way limiting the scope of the present disclosures, developments and/or solutions, a voltage carrier signal may be 50 mVrms at 100 kHz and a signal to be measured may be 100 μVrms at 10 Hz.

In an alternative exemplary implementation, parts of the multiplexing and/or demultiplexing logic may be implemented in software in combination with Analogue-to-Digital (ND) and Digital-to-Analogue (D/A) circuit elements. The software implementing these functions may be written in any high-level, or low-level, or intermediate programming languages.

Compared to known sensor array signal demultiplexing solutions, the present developments do not require any switching elements in array 100 to perform sensor multiplexing. Also, the generation of artifacts is strongly reduced by its continuous-time waveform operation compared to discrete-time TDMA scanning techniques. Moreover, the use of frequency and phase lock-in demodulation during FDMA de-multiplexing strongly reduces the equivalent noise bandwidth of the overall read-out system. Furthermore, the low-frequency noise contributions added by read-out circuits 107 can be filtered out through the appropriate selection of frequencies for each column line 104 of array 100. The result of these improvements are reflected onto lower complexity, improved performance, lower design and manufacturing costs, and higher density of sensor elements per $cm^2$ of silicon chip.

The above exemplary implementation descriptions are simplified and do not include hardware and software elements that are used in the implementations but are not part of the current developments, are not needed for the understanding of the implementations and/or developments, and are obvious to any user of ordinary skill in related art. Furthermore, variations of the described method, system architecture, and software architecture are possible, where, for instance, method steps, and hardware and software elements may be rearranged, omitted, or added.

Various implementations of the developments are described above in the Detailed Description. While these descriptions directly describe the above implementations, it is understood that those skilled in the art may conceive modifications and/or variations to the specific implementations shown and described herein. Any such modifications or variations that fall within the purview of this description are intended to be included therein as well. Unless specifically noted, the words and phrases in the specification and claims are to be given the ordinary and accustomed meanings to those of ordinary skill in the applicable art(s).

The foregoing description of preferred implementations and best mode of the developments known to the applicant at this time of filing the application have been presented and are intended for the purposes of illustration and description. It is not intended to be exhaustive or limit the developments to the precise form disclosed and many modifications and variations are possible in the light of the above teachings. The implementations were chosen and described in order to best explain the principles of the developments hereof and relative practical applications and to enable others skilled in the art to best utilize the developments hereof in various implementations and with various modifications as are suited to the particular use contemplated. Therefore, it is intended that the developments not be limited to the particular implementations disclosed for carrying out these developments, but that the developments hereof will include all implementations falling within the scope of the appended claims.

In one or more exemplary implementations, the functions described may be implemented in hardware, software, firmware, or any combination thereof. If implemented in software, the functions may be stored on or transmitted over as one or more instructions or code on a computer readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer or any other device or apparatus operating as a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed exemplary implementations is provided to enable any person skilled in the art to make or use the present developments. Various modifications to these exemplary implementations will be readily apparent to those skilled in the art, and the generic principles defined herein may be applied to other implementations without departing from the spirit or scope of the developments. Thus, the present developments are not intended to be limited to the implementations shown herein but is to be accorded the widest scope consistent with the principles and novel features disclosed herein.

The invention claimed is:

1. A method for multiplexing and demultiplexing sensor element signals in a two dimensional sensor array without using switching elements, the method comprising:
   for each column of sensor elements in the array, feeding a continuous voltage harmonic carrier waveform to all the sensor elements of the respective column of the sensor array, where a different continuous voltage harmonic carrier waveform is fed to each column;
   for each sensor element, feeding a signal to the respective sensor element, where a different signal is fed to each sensor element;
   for each row of sensor elements in the array, reading a summed output current from all sensor elements in the same row, where the summed output current comprises continuous current harmonic waveforms multiplexed with the signals fed to the sensor elements of the same row; and
   for each row of sensor elements in the array, recovering by lock-in demodulation the signals fed to each sensor element in the same row from the summed output current from all sensor elements in the same row.

2. The method of claim 1, further comprising subtracting all common current signal components not being modulated by the individual voltage signals to be measured from the summed continuous output currents from all sensor elements of each row.

3. The method according to claim 1, further comprising applying a constant voltage at each row of the array using individual or common voltage sources.

4. The method according to claim 1, further comprising converting the summed continuous output current at each row of the array into a continuous row voltage through individual or common capacitors.

5. The method according to claim 1, the different continuous voltage harmonic waveforms being applied to the columns of the array, differ in at least one of amplitude, frequency and phase characteristics among columns.

6. The method according to claim 1, the individual continuous current waveforms from each sensor element in the same row of the array, being demultiplexed from the summed continuous output current waveform of the same row using the differences in at least one of amplitude, frequency and phase characteristics among the individual current waveforms.

7. The method according to claim 1, the sensor elements in the array being GFET variable resistance transistor devices of the same or different types.

8. A two dimensional sensor array for multiplexing and demultiplexing sensor element signals without using switching elements, the sensor array comprising:
  transistor devices, the transistor devices being arranged in rows and columns, and each transistor's resistance being individually modulated by a signal fed at the transistor's gate;
  a plurality of voltage sources for feeding the column lines with a continuous voltage waveform;
  column lines, each column line connecting the source terminals of the transistor devices in the same column with a corresponding voltage source each source feeding a voltage waveform between the source terminal and the corresponding drain terminal of the transistor devices in the same column;
  row lines, each row line connecting the drain terminals of the transistor devices in the same row with a lock-in amplifier; and
  a plurality of lock-in amplifiers, each lock-in amplifier demultiplexing a summed continuous output current waveform in a row using differences in at least one of amplitude, frequency and phase characteristics among individual continuous current harmonic waveforms modulated by the continuous voltage waveform signals fed to the sensor elements of the same row, the summed continuous output current waveform comprising the continuous current harmonic waveforms.

9. The two dimensional sensor array according to claim 8, further comprising a current subtracting device connected at each row of the array for subtracting all common current signal components not being modulated by the individual voltage signals to be measured from the summed continuous output currents from all transistor devices of each row.

10. The two dimensional sensor array according to claim 8, the transistor devices being of the same or different types.

11. The two dimensional sensor array according to claim 8, further comprising a constant voltage source for each row of the array connected to the respective row line.

12. The two dimensional sensor array according to claim 8, further comprising a capacitor connected at each row of the array for converting the summed continuous output current at each row of the array into a continuous row voltage.

13. The two dimensional sensor array according to claim 8, the continuous voltage harmonic waveforms applied to the columns of the array, differing in at least one of amplitude, frequency and phase characteristics among columns.

14. The two dimensional sensor array according to claim 8, further comprising parts of the readout module being implemented in the digital domain and controlled by software code.

15. A non-transitory computer program product that causes a readout module of a sensor array to demultiplex sensor element signals, the sensor array having sensor elements arranged into an array, the non-transitory computer program product having instructions to:
  read the summed output continuous current waveforms from all sensor elements in the same row; and
  recover the individual continuous signals to be measured from the summed continuous output currents from all sensor elements in the same row by lock-in demodulation.

16. The non-transitory computer program product according to claim 15, further comprising instructions to subtract all common current signal components not being modulated by the individual voltage signals to be measured from the summed continuous output currents from all sensor elements of each row.

17. The non-transitory computer program product according to claim 15, further comprising instructions to apply a constant voltage at each row of the array.

18. The non-transitory computer program product according to claim 15, the individual current waveforms from each sensor element in the same row of the array, being demultiplexed from the summed output current waveform of the same row using the differences in at least one of amplitude, frequency and phase characteristics among the individual current waveforms.

19. The two dimensional sensor array according to claim 8, comprising manufacturing the transistor devices as GFET transistor devices using a method comprising:
  depositing a flexible polyimide substrate polymer layer on a sacrificial silicon wafer;
  defining a first layer of metallic tracks using a lift-off technique;
  transferring a single graphene layer from a growth substrate onto the polyimide substrate layer;
  defining the shape of the transistor channel by etching the graphene layer with oxygen plasma;
  depositing a second metal layer on top of the first metal layer and defining the second metal layer into the transistor's source and drain terminals using a lift-off technique;
  defining the active area on the transistor channel with an insulation layer, which insulation layer is defined into two insulator parts deposited on the transistor's source and drain;
  defining the polyimide substrate by reactive ion etching;
  depositing an electrolyte on the transistor's side opposite the substrate;
  positioning an Ag/Cl electrode inside the electrolyte, the Ag/Cl electrode forming the base of transistor.

20. The two dimensional sensor array according to claim 8, comprising manufacturing the two dimensional sensor array using a method comprising:
  creating a matrix of sensing elements where each sensing element is a GFET transistor device;
  depositing a flexible polyimide substrate polymer layer on a sacrificial silicon wafer;
  defining a first layer of metallic tracks using a lift-off technique;

transferring a single graphene layer from a growth substrate onto the polyimide substrate layer;
defining the shape of the transistor channels by etching the graphene layer with oxygen plasma;
depositing a second metal layer on top of the first metal layer and defining the second metal layer into the transistor's source and drain terminals using a lift-off technique;
defining the active area on the transistors' channels with an insulation layer, which insulation layer is defined into two insulator parts deposited on each transistor's source and drain;
defining the polyimide substrate by reactive ion etching;
depositing an electrolyte on the transistors' side opposite the substrates;
positioning an Ag/Cl electrode inside the electrolyte of each transistor, the Ag/Cl electrodes forming the bases of transistor.

* * * * *